(12) United States Patent
Wolter

(10) Patent No.: US 10,751,099 B2
(45) Date of Patent: Aug. 25, 2020

(54) BONE PLATE

(76) Inventor: Dietmar Wolter, Ahrensburg (DE)

( * ) Notice: Subject to any disclaimer, the term of this patent is extended or adjusted under 35 U.S.C. 154(b) by 78 days.

(21) Appl. No.: 14/342,856

(22) PCT Filed: Aug. 22, 2012

(86) PCT No.: PCT/EP2012/066353
§ 371 (c)(1),
(2), (4) Date: Mar. 5, 2014

(87) PCT Pub. No.: WO2013/037613
PCT Pub. Date: Mar. 21, 2013

(65) Prior Publication Data
US 2014/0214092 A1    Jul. 31, 2014

(30) Foreign Application Priority Data

Sep. 12, 2011   (EP) .................................... 11180964

(51) Int. Cl.
*A61B 17/80* (2006.01)
*A61B 17/86* (2006.01)
*F16B 39/34* (2006.01)

(52) U.S. Cl.
CPC .......... *A61B 17/8052* (2013.01); *A61B 17/80* (2013.01); *A61B 17/8057* (2013.01); *A61B 17/8605* (2013.01); *A61B 17/8033* (2013.01); *A61B 17/8047* (2013.01); *F16B 39/34* (2013.01); *Y10S 411/97* (2013.01)

(58) Field of Classification Search
CPC ............... Y10S 411/97; A61B 17/8033; A61B 17/8047; A61B 17/8052; A61B 17/8057; A61B 17/80; F16B 39/34
See application file for complete search history.

(56) References Cited

U.S. PATENT DOCUMENTS 3,294,139 A * 12/1966 Preziosi .................. F16B 39/34
118/408
3,741,205 A * 6/1973 Markolf ............. A61B 17/7059
606/291

(Continued)

FOREIGN PATENT DOCUMENTS

DE         19629011        1/1998
DE       102004035546      2/2006
(Continued)

OTHER PUBLICATIONS

Search Report.

*Primary Examiner* — David W Bates
*Assistant Examiner* — Marcela I Shirsat
(74) *Attorney, Agent, or Firm* — Alix, Yale & Ristas, LLP

(57) ABSTRACT

A bone plate has a through-hole that extends from an upper side to a bone-side underside of the bone plate. A lip is formed in the through-hole, which lip projects from the lateral surface of the through-hole and extends in the circumferential direction of the through-hole. The lip extends over part of the circumference of the through-hole. In a circumferential section of at least 120° that lies opposite the lip, the lateral surface is free of a lip. Material is reshaped only to a lesser extent compared to a lip that extends over the entire circumference of the through-hole. The risk of complications occurring due to deposited particles is reduced.

18 Claims, 5 Drawing Sheets

(56) References Cited

U.S. PATENT DOCUMENTS

| | | | | |
|---|---|---|---|---|
| 3,908,727 | A * | 9/1975 | Osborne | F16B 39/34 |
| | | | | 411/304 |
| 6,821,278 | B2 * | 11/2004 | Frigg | A61B 17/80 |
| | | | | 606/286 |
| 6,974,461 | B1 * | 12/2005 | Wolter | A61B 17/80 |
| | | | | 606/283 |
| 8,303,633 | B2 * | 11/2012 | Harris | A61B 17/7059 |
| | | | | 606/286 |
| 2005/0149026 | A1 * | 7/2005 | Butler | A61B 17/7059 |
| | | | | 606/71 |
| 2008/0051786 | A1 * | 2/2008 | Jensen | A61B 17/8057 |
| | | | | 606/86 A |
| 2008/0140130 | A1 * | 6/2008 | Chan | A61B 17/1728 |
| | | | | 606/280 |
| 2008/0300637 | A1 | 12/2008 | Austin | |
| 2010/0076496 | A1 * | 3/2010 | Fernandez | A61B 17/8057 |
| | | | | 606/297 |
| 2010/0082069 | A1 * | 4/2010 | Wolter | A61B 17/80 |
| | | | | 606/286 |
| 2011/0015681 | A1 | 1/2011 | Elsbury | |
| 2012/0071875 | A1 * | 3/2012 | Von Wieding | A61B 17/80 |
| | | | | 606/71 |

FOREIGN PATENT DOCUMENTS

| | | |
|---|---|---|
| DE | 102006062164 | 6/2008 |
| EP | 1649819 | 4/2006 |
| WO | WO2010076977 | 7/2010 |

* cited by examiner

BONE PLATE

BACKGROUND

The invention relates to a bone plate having a through-hole which extends from a top side to a bone-side underside of the bone plate. A lip is formed in the through-hole, said lip projecting from the lateral surface of the through-hole and extending in the circumferential direction of the through-hole.

Such bone plates are designed to be connected to a bone. They can be used for example to stabilize a bone following a fracture. To this end, the bone plate is positioned such that it extends across the fracture site and is then secured to the bone fragments. As a result, the fracture site is immobilized and the bone can heal. The bone plate can also be used for other purposes and be, for example, an element, to be connected to a bone, of an endoprosthesis.

In order to secure the bone plate to the bone, a bone screw is inserted into the through-hole, said bone screw being provided with a thread both on the shank and on the head. The shank of the screw passes so far into the bone material that the head of the screw passes into the through-hole in the bone plate. The head of the bone screw is dimensioned such that its outside diameter is larger than the smallest diameter of the plate hole, for example at the level of the material lip. As the bone screw is screwed in further, the lip is deformed such that a threaded connection is formed between the head of the bone screw and the lip in the through-hole in the bone plate. Since there is a threaded connection both between the shank of the bone screw and the bone material and between the head of the screw and the bone plate, a secure connection between the bone plate and the bone is established. Since the threaded connection between the head of the bone screw and the bone plate is formed only by a deformation process when the bone screw is screwed in, it is not necessary to screw the bone screw into the bone plate at a particular predetermined angle. Rather, the angle can be selected freely within particular limits. This gives the surgeon a high degree of flexibility during the operation.

In previous bone plates, the lip extends around the entire circumference of the through-hole. In order to establish a stable threaded connection, the screw is screwed so far into the lip until there is a threaded connection with the lip around the entire circumference of the screw head. In order to achieve this, the screw has to be screwed in an appreciable amount further after first coming into engagement with the lip, with the material of the lip being deformed to a considerable extent.

During each material deformation, there is the risk that small particles can be removed from the surface of the material. If these particles are distributed in the environment of the bone place and come into contact with the tissue, complications which hinder the progress of the healing process can occur.

SUMMARY

A bone plate is provided in which the risk of complications is reduced.

Briefly stated, the lip extends over a part of the circumference of the through-hole. A circumferential section, located opposite the lip, of the lateral surface is free of a lip, wherein the circumferential section extends over at least 120°.

A number of terms will first be explained. A lip denotes a region in which the material thickness is reduced compared with the material thickness of the bone plate. The lip projects from the lateral surface of the through-hole in the direction of the center of the through-hole. The lip has a longitudinal extent along the circumference of the through-hole.

When the lateral surface is free of a lip in a section located opposite the lip, this means that a screw head, which is inserted into the through-hole and is in contact with the lip on one side, is in direct contact with the lateral surface of the through-hole on the other side.

Since the lip extends only along a part of the circumference of the through-hole, material deformation takes place only in this region. The further the screw head engages into the lip, the greater becomes the force with which the screw head is pressed against the opposite lateral surface. Since the screw head enters into a threaded connection with the lip on one side and is pressed against the lateral surface on the other side, the screw head is fixed securely in the through-hole. However, compared with a lip which extends around the entire circumference of the through-hole, material is deformed only to a much lesser extent. The risk of complications occurring on account of removed particles drops to the same extent.

On the other side of the through-hole, the screw head is intended to rest as flat as possible against the lateral surface, in order to be retained securely. This requires that a sufficiently large section of the lateral surface is free of a lip. Preferably, the cohesive circumferential section in which the lateral surface is free of a lip extends over at least 180°, more preferably over at least 240°. The remaining circumference of the through-hole can have a continuous lip. A lip composed of a plurality of sections is also possible.

In a preferred embodiment, the lip has a step arranged between the lateral surface of the through-hole and a central region of the lip, said step extending along the lip. The lip then has in a central region a section in which the material thickness is low. The bone screw which engages in this section of the lip first of all has to displace only a little material. Nevertheless, there is secure guidance directly after the first engagement, and so the bone screw moves along a defined path when it is screwed in further. Only when the bone screw penetrates into the region of the step does more material have to be displaced. The threaded connection between the head of the bone screw and the lip is thus formed in two stages. In a first stage, the head thread engages in a region with a low material thickness, such that the first engagement takes place easily and with little expenditure of force. Only when the head thread has penetrated into the region of the step is so much material displaced that the threaded connection achieves sufficient stability.

When the lip is provided with a step, this means that, proceeding outward in the radial direction from the center, the lip has a greater gradient in the region of the step then in the region of the central section. Proceeding from the center of the through-hole, the step follows the central section in the peripheral direction. The gradient denotes the angle which the top surface or bottom surface of the lip encloses with the plane extending transversely to the axial direction of the through-hole.

It may likewise be advantageous for the engagement of the screw in the lip if the lip is formed in an undulating manner in the circumferential direction. If the top surface of the lip has an inclination face that is inclined in the circumferential direction, a movement which follows the undulation in the circumferential direction has an upward component in the direction of the top side of the bone plate and a downward component in the direction of the underside of the bone plate. This has the advantage that first contact takes place at a less acute angle when the head thread of the screw meets the inclination face. On account of the less acute angle, the risk of the thread sliding along the top surface of the lip instead of cutting into the lip and deforming the latter is reduced. The threaded connection between the bone screw and the bone plate is thus formed in exactly that position which the bone plate is in when the thread first engages in the lip.

It is advantageous if the bone screw head screwed into the bone plate projects as little as possible beyond the bone plate, since otherwise there is the danger of the surrounding tissue being irritated. If the lip is arranged in the (lower) half, adjoining the underside of the bone plate, of the through-hole, there is space above the lip for countersinking the head of the bone screw in the bone plate. The (upper) half, adjoining the top side of the bone plate, of the through-hole is then formed by the lateral surface of the through-hole, and is thus free of the lip.

The bone plate having the lip in the through-hole can be formed in one piece. Alternatively, it is possible for a region surrounding the through-hole and in the form of an inlay to be inserted into the bone plate. The inlay with the lip can be formed initially as a separate part and then be connected to the bone plate. In order to make it easier to form the threaded connection, the inlay can consist of a softer material than the bone plate.

In order to allow the surgeon optionally to use conventional bone screws, the head of which is not provided with a thread, the lateral surface of the through-hole can be widened outwardly above the lip. This region of the lateral surface can then form a mating surface for a conventional screw head. In cross section, the widening can be for example in the form of a segment of a circle.

The invention also relates to a system composed of such a bone plate and a bone screw. The bone screw has a head thread which is designed to deform the lip in the through-hole, in order to form a threaded connection. In order to allow secure fastening to the bone, the bone plate generally has a plurality of through-holes. Accordingly, the system can also comprise a plurality of bone screws.

The material deformation that takes place during the formation of the threaded connection is not intended as far as possible to be associated with chip abrasion. Tests have shown that chip abrasion is kept low if the screw head has a conical lateral surface and the angle which the lateral surface encloses with the screw axis is between 19° and 28°.

BRIEF DESCRIPTION OF THE DRAWINGS

The invention is described by way of example by way of advantageous embodiments in the following text with reference to the appended drawings, in which.

DETAILED DESCRIPTION

Figure 1:
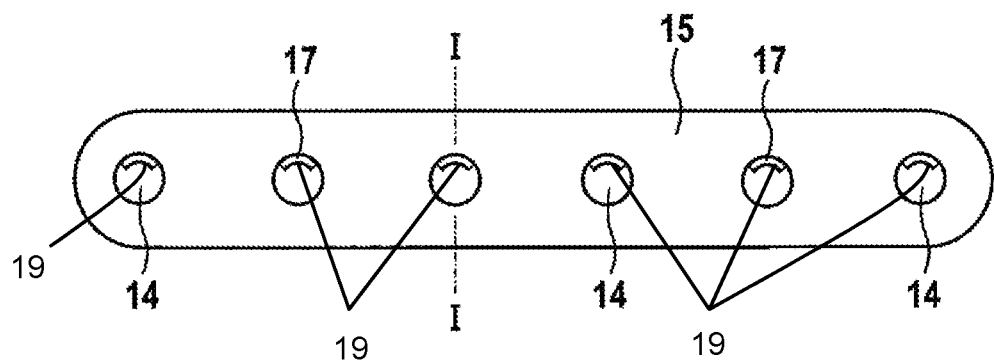
FIG. 1 shows a view from above of a bone plate.
Figure 2:
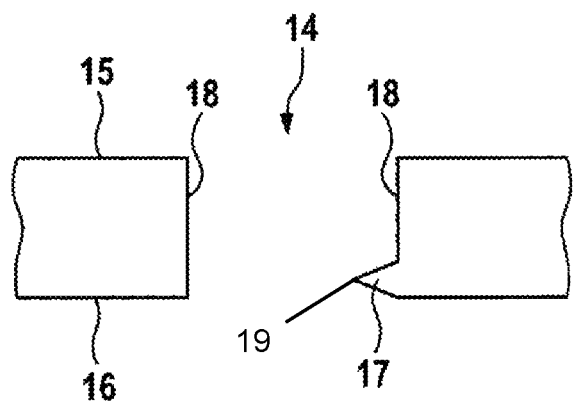
FIG. 2 shows a section through FIG. 1 along the line I-I.

According to FIGS. 1 and 2, a bone plate has six through-holes 14, which extend from a top side 15 of the bone plate to an underside 16 of the bone plate. A lip 17 is formed around a part of the circumference in each through-hole 14, said lip 17 projecting from the lateral surface 18 in the direction of the center of the through-hole 14. The lip 17 extends along the lateral surface 18 around a circumferential section of 180°. In the remaining circumferential section of the lateral surface of 180°, there is no lip. The lip 17 extends radially from the lateral surface 18 to an innermost edge 19. In the depicted embodiment the innermost edge 19 maintains a constant radius relative to the center of the through-holes 14. The lip 17 terminates with the underside 16 of the bone plate, such that as much room as possible for receiving the screw head remains above the lip 17.

The bone plate is intended to be placed with its underside 16 on a bone, such that the bone plate extends across a fracture site of the bone. Once the bone has been repositioned in the correct position, the bone plate is connected to the bone fragments. The bone is then fixed in this position and can heal.

Figure 7:
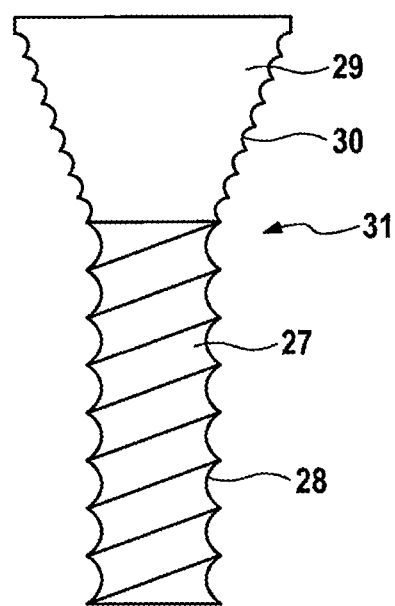
FIG. 7 shows a bone screw intended for the bone plate.

In order to connect the bone plate to the bone, bone screws 31 are used, as are illustrated in FIG. 7. The bone screws 31 have a shank 27, which is provided with a bone thread 28, and a screw head 29, the outer surface of which has a head thread 30 with a smaller gradient. The lateral surface of the screw head 29 encloses an angle of 25° with the screw axis. The bone screw is screwed into the bone until the screw head 29 passes into the through-hole 14. In this case, the angle which the bone screw encloses with the axis of the through-hole can be selected freely between about 0° and 15°. If the bone screw is now screwed in further, the head thread 30 of the bone screw 31 comes into engagement with the lip 17.

In this case, firstly the lip 17 is deformed such that a threaded connection is formed between the head 29 of the bone screw 31 and the lip 17. In addition, on account of the increasing pressure which arises during screwing into the lip 17, the screw head 29 is pushed against the lateral surface 18 on the opposite side of the through-hole 14.

In order to make it easier to form the threaded connection, the bone screw 31 can be composed of a harder material than the bone plate. For example, the bone plate may be produced from pure titanium, while the bone screw 31 is composed of the titanium alloy TiAl6V4.

Figure 3:
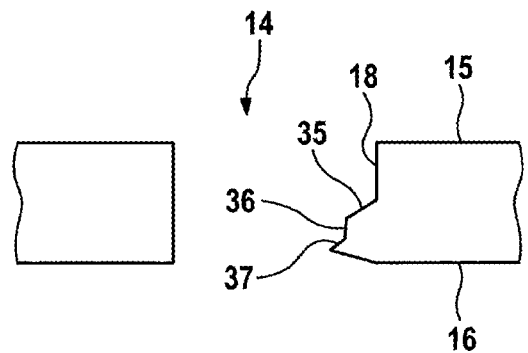
FIG. 3 shows the view from FIG. 2 in another embodiment.

According to FIG. 3, the lip 17 comprises a peripheral region 35, a step 36 and a central region 37. In the peripheral region 35 and the central region 37, the gradient of the lip surface is small and is for example about 15°. In the region of the step 36, which connects the central region 37 and the peripheral region 35, the gradient is much greater and is for example 75°.

If a bone screw 31 is screwed into the through-hole 14, the head thread 30 first of all comes into engagement with the central region 37 of the lip 17. In the central region 37, the lip is thin so that only a little material is displaced when the head thread 30 passes in. The surgeon who is screwing in the screw scarcely notices increased resistance. When the screw is screwed in further, the head thread 30 passes further into the central region 37 and approaches the step 36. When the head thread 30 arrives at the step 36, the thread has already been formed to such an extent that it provides secure guidance for the bone screw. When the head thread 30 bears against the step 36, the resistance which has to be overcome when the screw is screwed in further increases, since now a greater quantity of material has to be deformed. From the point of increased resistance, the bone screw 31 is screwed in further through 90°, such that on one side a stable threaded connection is formed and on the other side the screw head 29 is pressed with sufficient force against the lateral surface 18. Thus, the final state is achieved and the head thread 30 is locked securely in the lip 17.

Figure 4:
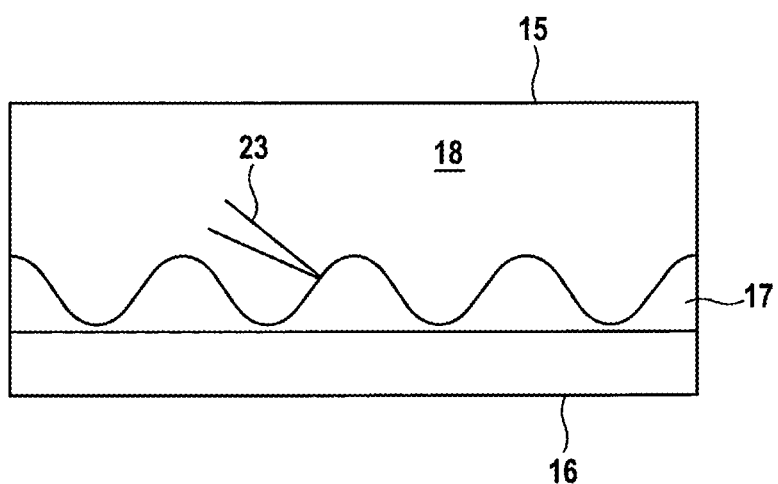
FIG. 4 shows a view from the center of the through-hole in the direction of the lateral surface in yet another embodiment.
Figure 8:
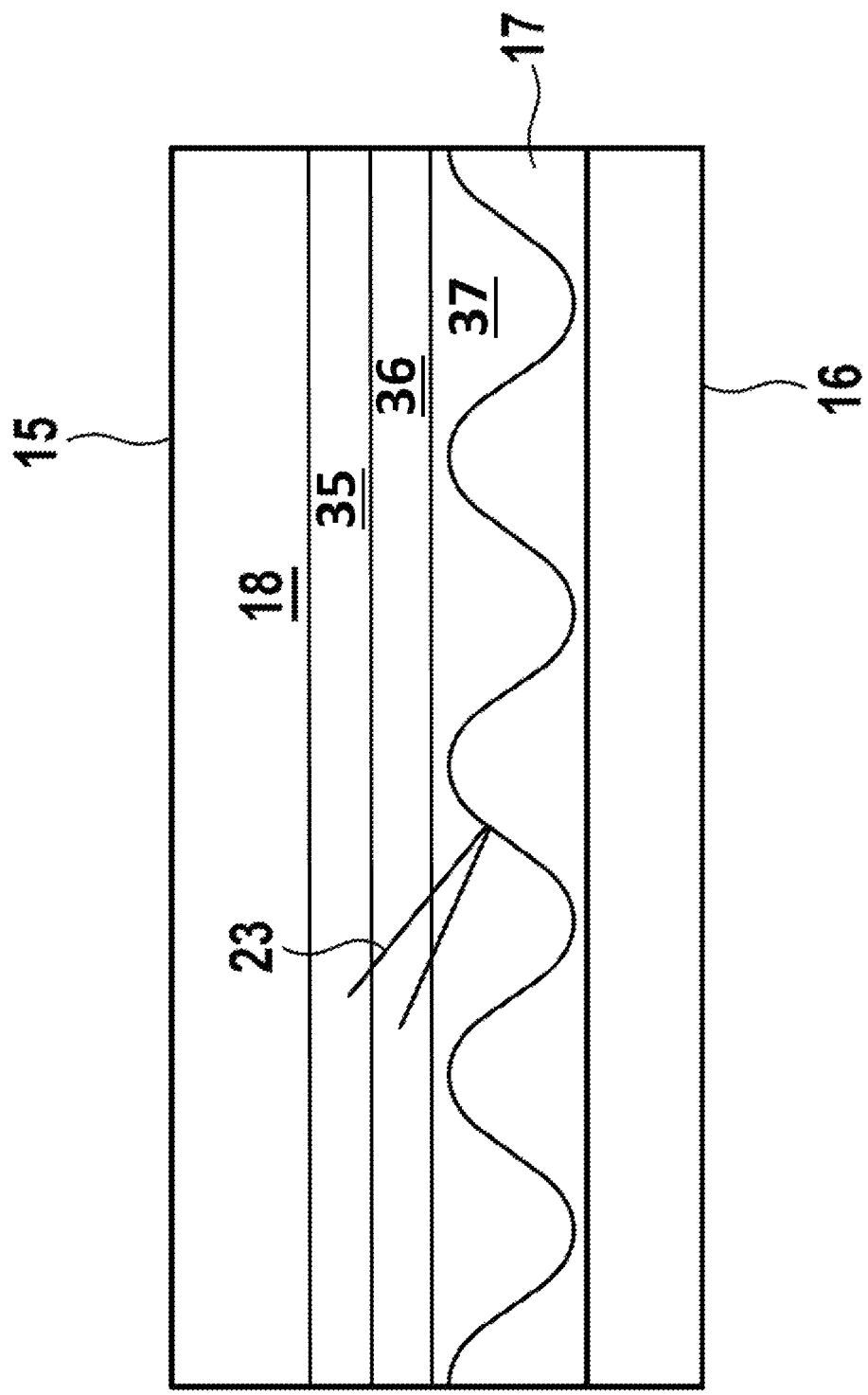
FIG. 8 shows the view from FIG. 4 of another embodiment.

FIG. 4 shows a view in which a plan view of the lateral surface 18, as seen from the center of the through-hole 14, is projected into the plane. That region of the lateral surface which is free of the lip 17 is not visible in FIG. 4. In this embodiment, the lip 17 is in an undulating form. When the bone screw is screwed in, the first thread turn of the head thread comes into contact with the lip 17 at a particular point in time. Since the thread turn approaches the lip 17 obliquely from above, as indicated at 23 in FIG. 4, there is a high probability that first contact between the head thread and the lip 17 will take place in a region having a large gradient. The thread turn then meets the surface of the lip 17 substantially at right angles, such that the thread turn can immediately cut into the lip 17 and deforms the latter. A threaded connection is formed in the region of the lip 17, this simultaneously having the result that the screw head 29 is pressed against the lateral surface on the other side of the through-hole 14. As a result, the screw head 29 is locked securely in the through-hole 14. FIG. 8 shows a similar plan view of the lateral surface 18, in an embodiment which includes a peripheral region 35, a step 36, and a central region 37. As with FIG. 4, this embodiment provides a high probability that the thread turn will meet the surface of the lip 17 at substantially right angles. Additionally, the lip, requiring little material displacement, allows the thread to be formed so as to provide secure guidance prior to bearing against the step 36.

Figure 5:
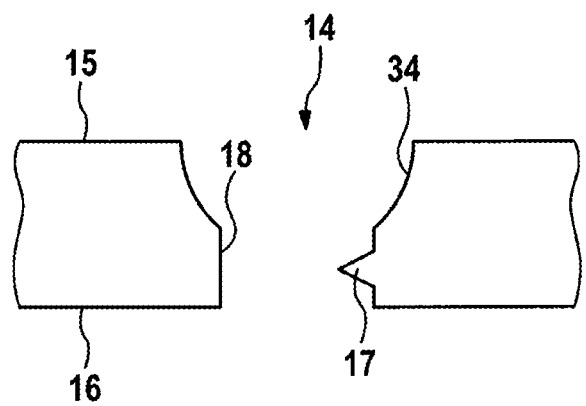
FIGS. 5 and 6 show the view from FIG. 2 in further embodiments.

In FIG. 5, the lateral surface 18 has a widening 34 above the lip 17, said widening having the form of a segment of a circle in cross section. In this embodiment, it is optionally possible to use conventional bone screws, the head of which is free of a thread. The widening 34 then forms a mating surface for a bone screw having a hemispherical head, such that the bone screw can be inserted into the through-hole 14 at different angles.

Figure 6:
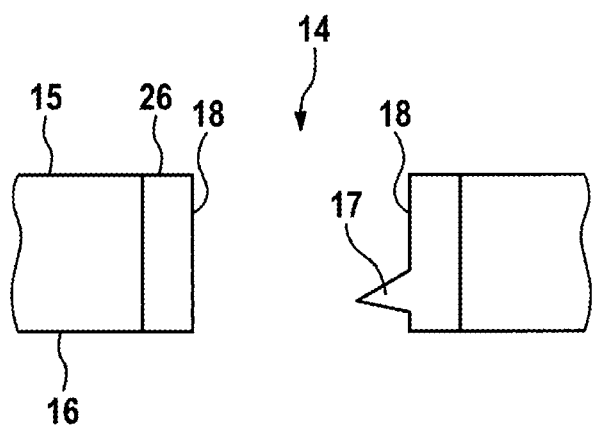

FIG. 6 shows an embodiment in which an inlay has been inserted into the bone plate. The inlay 26 is composed of a softer material than the bone plate and forms the lip 17 and also the surround of the through-hole 14.

The invention claimed is:

1. A bone plate system comprising:
a bone screw having a central screw axis extending along the bone screw in a longitudinal direction; and
a bone plate having a through-hole with a circumference surrounding a central through-hole axis and having a circumferential section which extends from a top side to a bone-side underside of the bone plate, wherein the through-hole substantially circular shape, wherein a lip is formed in the through-hole, said lip projecting from a lateral surface of the through-hole and extending in a circumferential direction of the through-hole, characterized in that the lip extends over a part of the circumference of the through-hole, and in that the lateral surface in the circumferential section located opposite the lip is free of a lip, wherein the circumferential section located opposite the lip extends continuously over at least 240° measured with respect to the central through-hole axis, the bone screw has a head thread which is configured to deform the lip in the through-hole creating a threaded connection between the head thread and the lip, and the bone screw configured to be mounted in the bone plate such that the central screw axis is tilted at an angle relative to the through-hole axis.

2. The bone plate system as claimed in claim 1, characterized in that the lip is integrally formed in the through-hole.

3. The bone plate system as claimed in claim 2, characterized in that the lip is arranged in that half of the through-hole that is adjacent to the underside of the bone plate.

4. A system composed of a bone plate as claimed in claim 2 and a bone screw, wherein the bone screw has a head thread which is configured to deform the lip in the through-hole.

5. The bone plate system as claimed in claim 1, characterized in that the lip is arranged in a half of the through-hole that is adjacent to the underside of the bone plate.

6. A system composed of a bone plate as claimed in claim 5 and a bone screw, wherein the bone screw has a head thread which is configured to deform the lip in the through-hole.

7. The bone plate system as claimed in claim 1, wherein the through-hole is provided in an inlay.

8. A system composed of a bone plate as claimed in claim 7 and a bone screw, wherein the bone screw has a head thread which is configured to deform the lip in the through-hole.

9. A system composed of a bone plate as claimed in claim 1 and a bone screw, wherein the bone screw has a head thread which is configured to deform the lip in the through-hole.

10. The bone plate system as claimed in claim 1, characterized in that the bone screw has a head with a conical lateral surface and an axis, wherein the lateral surface comprises an angle of between 19° and 28° with the central screw axis.

11. The bone plate system as claimed in claim 1, characterized in that the lip is formed in an undulating manner in the circumferential direction.

12. A bone plate system as claimed in claim 1, wherein the angle of the central screw axis relative to the through-hole axis is between 0° and 15°.

13. A bone plate system comprising:
a bone screw having a central screw axis extending along the bone screw in a longitudinal direction; and
a bone plate having a circular through-hole with a circumference surrounding a central through-hole axis of the through-hole and having a circumferential section which extends from a top side to a bone-side underside of the bone plate, wherein a lip is formed in the through-hole, said lip projecting from a lateral surface of the through-hole and extending in a circumferential direction of the through-hole, characterized in that the lip extends over a part of the circumference of the through-hole, and in that the lateral surface in the circumferential section located directly opposite the lip is free of a lip, wherein the circumferential section located directly opposite the lip extends continuously over at least 240° measured with respect to the central through-hole axis, the bone screw has a head thread which is configured to deform the lip in the through-hole creating a threaded connection between the head thread and the lip, and the bone screw configured to be mounted in the bone plate such that the screw axis is tilted at an angle relative to the through-hole axis.

14. The bone plate system as claimed in claim 13, characterized in that the lip has a step and a central region, said central region is oriented toward the center of the through-hole, said step is arranged between the lateral surface of the through-hole and the central region of the lip, and said step extends along the lip.

15. The bone plate system as claimed in claim 13, characterized in that the lip is formed in an undulating manner in the circumferential direction.

16. The bone plate system as claimed in claim 13, characterized in that the lip is arranged in a half of the through-hole that is adjacent to the underside of the bone plate.

17. A bone plate system comprising:
a bone screw having a central screw axis extending along the bone screw in a longitudinal direction; and
a bone plate having a through-hole with a circumference surrounding a central through-hole axis and having a circumferential section which extends from a top side to a bone-side underside of the bone plate, wherein a lip is formed in an undulating manner in a circumferential direction in the through-hole, said lip projecting from a lateral surface of the through-hole and extending in the circumferential direction of the through-hole, said lip having a central region oriented toward the center of the through-hole and a step, said step arranged between the lateral surface of the through-hole and the central region of the lip and extending along the lip, characterized in that the lip extends over a part of the circumference of the through-hole, and in that the lateral surface in the circumferential section located opposite the lip is free of a lip, wherein the circumferential section located opposite the lip extends continuously over at least 240°, the bone screw has a head thread which is configured to deform the lip in the through-hole creating a threaded connection between the head thread and the lip, and the bone screw configured to be mounted in the bone plate such that the screw axis is tilted at an angle relative to the through-hole axis.

18. The bone plate system as claimed in claim 17, characterized in that the lip is arranged in a half of the through-hole that is adjacent to the underside of the bone plate.

\* \* \* \* \*